US010295520B2

(12) United States Patent
Letts et al.

(10) Patent No.: US 10,295,520 B2
(45) Date of Patent: May 21, 2019

(54) METHODS AND APPARATUS FOR TESTING FUEL MATERIALS FOR EXOTHERMIC REACTIONS

(71) Applicant: IH IP Holdings Limited, Raleigh, NC (US)

(72) Inventors: Dennis G. Letts, Austin, TX (US); John Dewey Weaver, III, Raleigh, NC (US)

(73) Assignee: IH IP Holdings Limited, St. Helier (JE)

( * ) Notice: Subject to any disclaimer, the term of this patent is extended or adjusted under 35 U.S.C. 154(b) by 173 days.

(21) Appl. No.: 15/617,347

(22) Filed: Jun. 8, 2017

(65) Prior Publication Data
US 2018/0196026 A1 Jul. 12, 2018

Related U.S. Application Data

(60) Provisional application No. 62/347,924, filed on Jun. 9, 2016.

(51) Int. Cl.
| | |
|---|---|
| G01N 25/00 | (2006.01) |
| G01K 15/00 | (2006.01) |
| G01K 17/00 | (2006.01) |
| G01K 3/00 | (2006.01) |
| G01N 33/22 | (2006.01) |
| G01N 25/20 | (2006.01) |

(52) U.S. Cl.
CPC ............ *G01N 33/22* (2013.01); *G01N 25/20* (2013.01)

(58) Field of Classification Search
USPC ........................................ 374/45, 1, 31, 112
See application file for complete search history.

(56) References Cited

U.S. PATENT DOCUMENTS

| | | | |
|---|---|---|---|
| 6,623,976 B1 * | 9/2003 | Hale ...................... | G01N 27/16 374/37 |
| 2015/0377807 A1 * | 12/2015 | Grass ................... | G01N 33/225 374/36 |
| 2018/0374587 A1 * | 12/2018 | Letts ..................... | B01J 19/087 |

* cited by examiner

*Primary Examiner* — Mirellys Jagan
(74) *Attorney, Agent, or Firm* — NK Patent Law

(57) ABSTRACT

Methods and apparatus are disclosed for testing simultaneously multiple fuel materials for suitability of producing excess heat. In some embodiments, multiple fuel materials are placed on a substrate with a thermoelectric converter inserted in between each fuel material and the substrate. When a triggering condition is applied, exothermic reactions may be triggered in some of the fuel materials. The voltage output of the thermoelectric converters is a direct measurement of the temperature of each fuel material, which is an indicator of whether an exothermic reaction is taking place in the fuel material. A known fuel material may be included in the testing array to establish the baseline of voltage readings.

22 Claims, 4 Drawing Sheets

METHODS AND APPARATUS FOR TESTING FUEL MATERIALS FOR EXOTHERMIC REACTIONS

CROSS-REFERENCE TO RELATED APPLICATION

This application claims the benefit of priority of U.S. Provisional Patent Application No. 62/347,924, titled "METHODS AND APPARATUS FOR TESTING FUEL MATERIALS FOR EXOTHERMIC REACTIONS" filed on Jun. 9, 2016 which is incorporated herein in its entirety by this reference.

TECHNICAL FIELD

The present disclosure relates generally to testing apparatus and methods for selecting suitable fuel materials for exothermic reactions, and, more specifically, to testing devices configured to testing multiple fuel materials simultaneously.

BACKGROUND

Over the past several decades, excess heat generation phenomena have been observed under different settings and in different systems. Generally, an excess heat generation system comprises a transition metal loaded with hydrogen or deuterium. In certain cases and under certain conditions, the amount of output power significantly exceeded the amount of input power used for operating the heat generation system.

In attempts to reproduce the reported excess heat generation experiments, scientists have tried different materials in combination with different conditions. However, most of the reported excess heat generation phenomena have remained elusive. They are difficult to reproduce and to calibrate.

The present disclosure teaches advanced devices and methods for testing multiple fuel materials simultaneously to shorten the material selection process and to improve the efficiency of the verification process.

SUMMARY

The present disclosure relates to advanced devices and methods configured to test simultaneously multiple fuel materials for excess heat generation reactions.

In some embodiments, a device for selecting one or more fuel materials suitable for producing excess heat in an exothermic reaction comprises a substrate and a plurality of thermoelectric converters. The substrate is configured to hold two or more fuel materials. Each of the plurality of thermoelectric converters is placed in between one fuel material and the substrate, and is configured to generate an output voltage that is proportional to the temperature difference between the substrate and the fuel material. The suitability of the fuel material for the exothermic reaction is determined based on the output voltage generated by the thermoelectric converter placed between the substrate and the fuel material when a reaction condition is applied. In one embodiment, the reaction condition includes a pressure and a temperature that trigger the exothermic reaction.

In one embodiment, when the output voltage from a thermoelectric converter exceeds a threshold, it is determined that the fuel material to which the thermoelectric converter is connected to may be suitable for the exothermic reaction. The threshold varies depending on the type of exothermic reactions that are triggered by the reaction condition.

In one embodiment, a known fuel material is used for calibration purpose and the threshold is set to be the voltage output by this calibration fuel material under the same calibration condition.

In some embodiments, a method for testing two or more fuel materials for suitability of producing excess heat in an exothermic reaction. The method comprises arranging the two or more fuel materials on a substrate and controlling the temperature of the substrate. Between each fuel material and the substrate, a thermoelectric converter is placed. The thermoelectric converters are configured to generate an output voltage as a measurement of the temperature difference between the substrate and the fuel materials. The method further comprises applying a reaction condition. The reaction condition is designed to trigger an exothermic reaction in at least one of the two or more fuel materials. The output voltages of the plurality of thermoelectric converters is monitored to determine the suitability of the fuel materials for the exothermic reaction.

DETAILED DESCRIPTION

Figure 1:
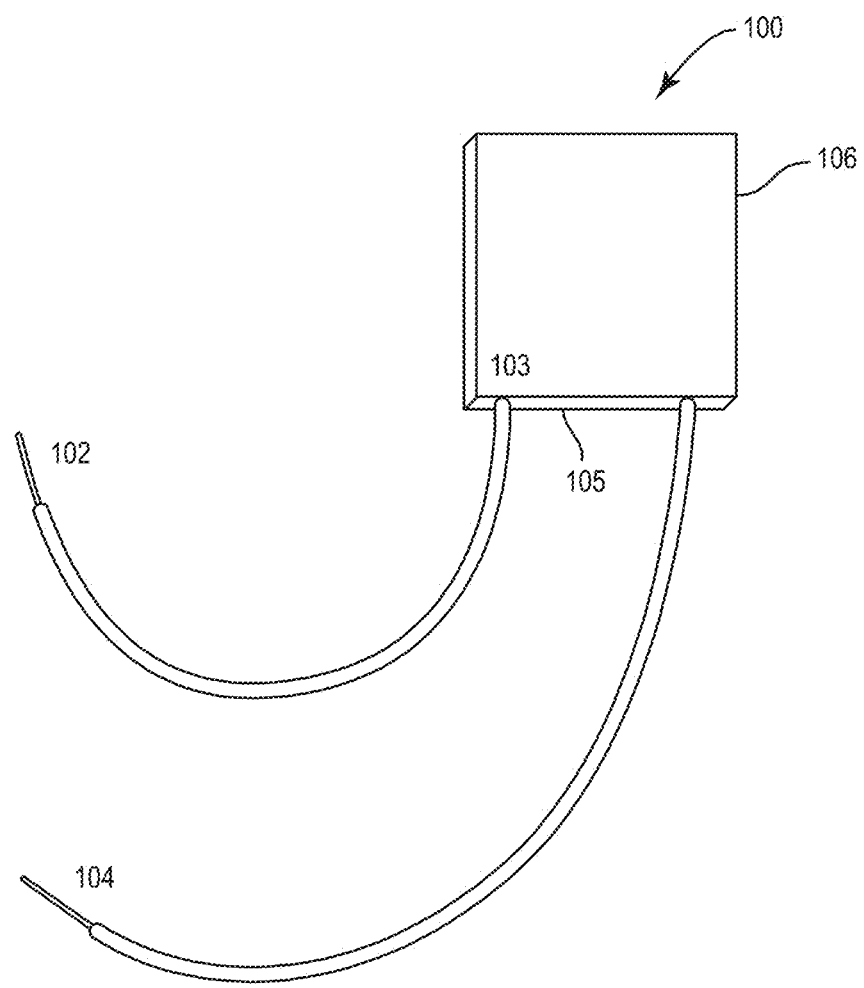
FIG. 1 illustrates an exemplary thermoelectric converter.

In referring to FIG. 1, an exemplary thermoelectric converter 100 comprises a body 106 and two electric leads 102 and 104. The electric leads 102 and 104 generate a voltage reading that is indicative of the temperature difference between the front and back surfaces, 103 and 105, of the body 106. The thermoelectric converter 100 is configured to generate an electric signal that is proportional to the temperature gradient between the front and back surfaces, 103 and 105, of the body 106, when within the operating range of the thermoelectric converter 100. Based on calibration data, the voltage output can be converted into a measurement of the temperature difference between the surfaces 103 and 105.

Figure 2:
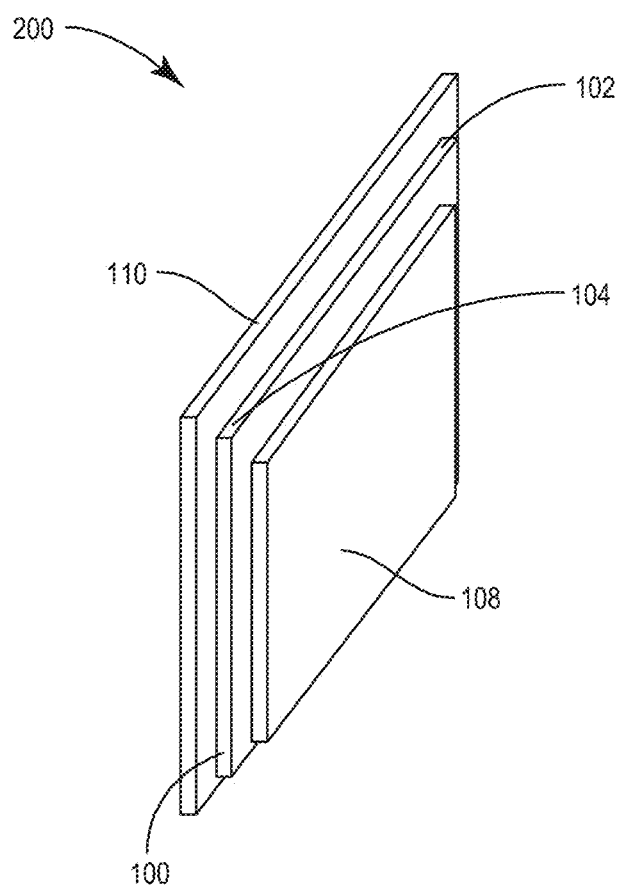
FIG. 2 illustrates an exemplary testing unit for testing an exothermic reaction fuel material.

FIG. 2 illustrates a testing unit 200 comprising a thermoelectric converter 100 configured to measure the exothermic effect of a testing reaction material. The testing unit 200 comprises a thermoelectric converter 100, a fuel material 108 and a substrate 110. The thermoelectric converter 100 comprises two electric leads, 102 and 104, that generate a voltage output that measures the difference between the temperature of the substrate 110 and that of the fuel material 108. Based on calibration data, the voltage output of the thermoelectric converter 100 can be converted into the temperature difference between the substrate 110 and the fuel material 108. When the temperature of the substrate 110 is kept constant, the voltage output of the thermoelectric converter 100 directly reflects the temperature of the fuel material 108.

When the fuel material 108 is involved in an exothermic reaction, heat is generated and the temperature of the fuel material 108 rises as a result. When the substrate 110 is kept at a constant temperature, the temperature difference between the fuel material 108 and the substrate 110 indicates whether the fuel material 108 is involved in an exothermic reaction. The temperature difference also indicates the efficacy of the exothermic reaction. The temperature of the fuel material 108 reflects the amount of excess heat generated during the exothermic reaction.

In excess heat generation experiments, it is well-known that reproducibility is difficult to achieve and finding the appropriate fuel material requires many time-consuming experiments repeated under the same reaction condition testing different materials. The present disclosure teaches an advanced device that can be used to test multiple materials for their efficacy as fuels in exothermic reactions.

Figure 3:
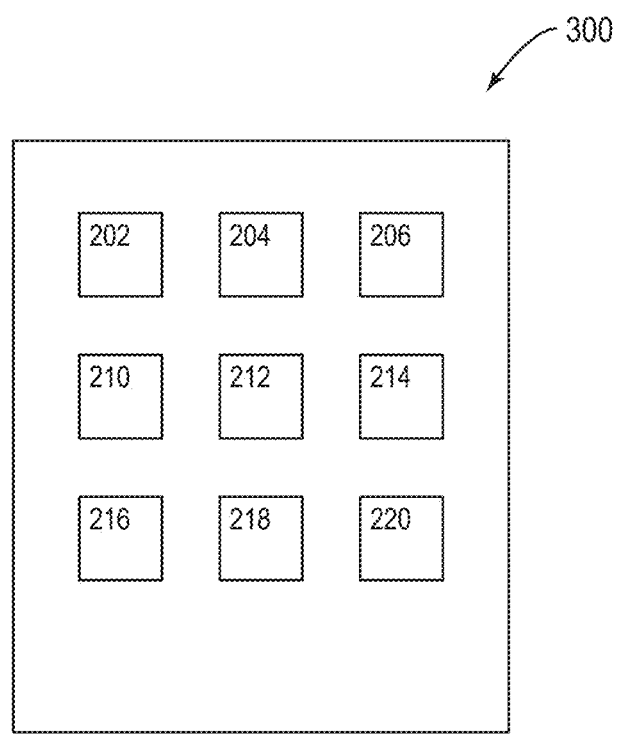
FIG. 3 illustrates a block diagram illustrating a testing array for testing multiple reaction materials simultaneously.

As shown in FIG. 3, a testing array 300 comprises multiple testing units, 202, 204 . . . 220. The testing array 300 comprises a substrate on which the multiple testing units are placed. Each testing unit comprises a fuel material to be tested for efficacy in sustaining an exothermic reaction and a thermoelectric converter that is placed in between the substrate and the fuel material. The substrate is maintained at a constant temperature. The temperature difference between the substrate and the fuel material is measured by the voltage output of the thermoelectric converter.

When the testing array is placed in a normal environment, the voltage outputs from thermoelectric converters are zero because the substrate and the fuel materials are both of the ambient temperatures. When the testing array is placed in a reaction chamber and a triggering condition is applied, the testing fuel material in one or more testing units in the testing array 300 may start an exothermic reaction. The excess heat generated in the exothermic reaction heats up the testing fuel material. The increase of the voltage output of the thermoelectric converter reflects the temperature change in the fuel material and is proportional to the amount of excess heat generated during the exothermic reaction.

In some embodiments, the triggering condition includes imposing a pre-determined environment. For example, in one embodiment, an electric field of a pre-determined magnitude may be applied. In another embodiment, a magnetic field of a pre-determined magnitude and/or polarity may be applied. In some embodiments, certain temperatures and pressures conducive to triggering a specific type of exothermic reaction may be applied as well. Other triggering conditions may include applying RF pulsing, AC current to induce glow discharge, DC current to generate plasma, etc.

In some embodiments, a known fuel material may be placed in one of the testing units for calibration purposes. The known fuel material may be calibrated beforehand to establish the temperature change due to a particular exothermic reaction. This temperature change can be used as a baseline to calibrate other testing fuel materials. When the voltage output of a thermoelectric converter for a particular testing fuel material is higher than that of the known fuel material, it may be determined that the particular testing fuel material is suitable for this particular exothermic reaction. When the voltage output from a testing fuel material is lower than that of the known fuel material, it may be determined that the testing fuel material is not suitable.

In one embodiment, a known fuel material may be tested for a type of exothermic reactions, e.g., Low Energy Nuclear Reaction (LENR). The voltage output from the known fuel material may be established as the threshold for this type of exothermic reactions. When testing, the voltage output from a testing unit, for example, testing unit 202, in the testing array 300 is compared to the threshold. If the voltage output is higher than the threshold, the fuel material in the testing unit 202 may be classified as suitable for this type of exothermic reactions. Otherwise, the fuel material in the testing unit 202 may be classified as unsuitable for this type of exothermic reactions.

Figure 4:
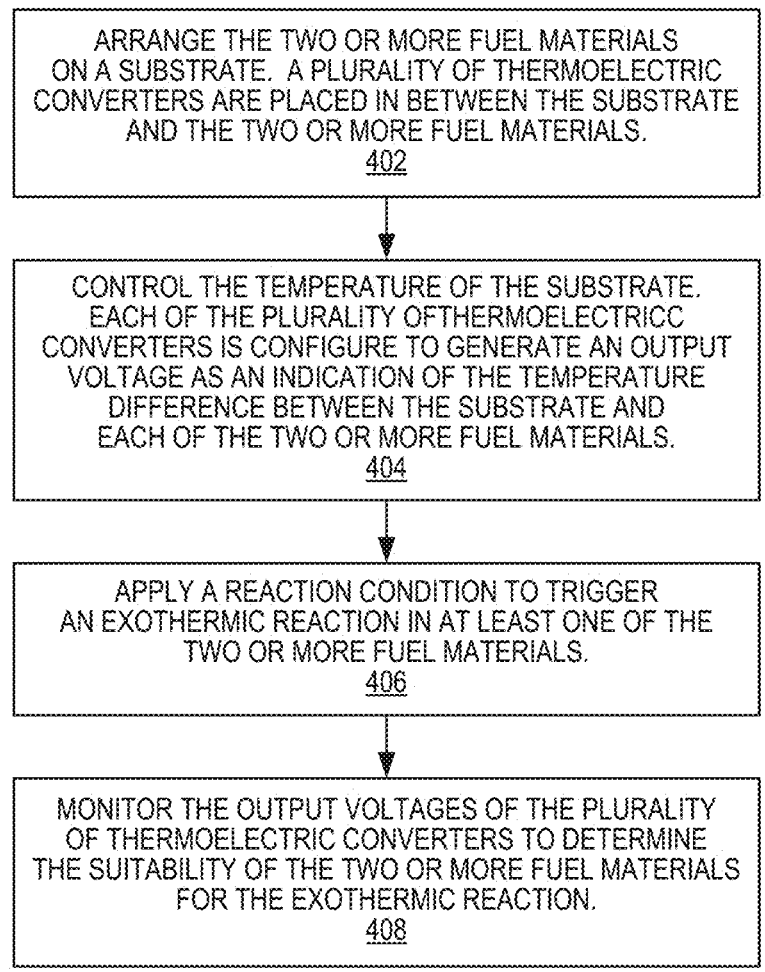
FIG. 4 is a flow chart illustrating an exemplary method of testing reaction materials using a testing array.

FIG. 4 is a flow chart illustrating an exemplary method for testing a plurality of fuel materials using the testing array 300. In step 402, two or more fuel materials are arranged on a substrate. A plurality of thermoelectric convertors are placed in between the substrate and each of the two or more fuel materials. In step 404, the temperature of the substrate is controlled and maintained at a certain level. Each of the plurality of thermoelectric converters is configured to generate an output voltage as an indicator of the temperature difference between the substrate and each of the two or more fuel materials. In step 406, a triggering condition is applied. The triggering condition is designed to trigger an exothermic reaction in some of the two or more fuel materials. In step 408, the voltage output of the plurality of thermoelectric converters are monitored. The voltage outputs are used to determine the suitability of the fuel materials in testing array 300 for the exothermic reaction.

The present invention may be carried out in other specific ways than those herein set forth without departing from the scope and essential characteristics of the invention. The present embodiments are, therefore, to be considered in all respects as illustrative and not restrictive, and all changes coining within the meaning and equivalency range of the appended claims are intended to be embraced therein.

What is claimed is:

1. A method for testing two or more fuel materials for suitability of producing excess heat in an exothermic reaction, comprising:
    arranging the two or more fuel materials on a substrate, wherein a respective one of a plurality of thermoelectric converters are placed in between the substrate and a respective one of the two or more fuel materials;
    controlling the temperature of the substrate, wherein each respective one of the plurality of thermoelectric converters is configured to generate an output voltage based on the temperature difference between the substrate and each of the two or more fuel materials;
    applying a triggering condition to the substrate, wherein the triggering condition is designed to trigger an exothermic reaction in one of the two or more fuel materials; and
    monitoring the output voltages of the plurality of thermoelectric converters to determine the suitability of each of the two or more fuel materials for the exothermic reaction during a reaction condition.

2. The method of claim 1, wherein the reaction condition includes a pressure and a temperature that trigger the exothermic reaction.

3. The method of claim 1, wherein applying a triggering condition comprises applying an electric field of a predetermined magnitude.

4. The method of claim 1, wherein applying a triggering condition comprises applying an electric field of a predetermined magnitude and polarity.

5. The method of claim 1, wherein applying a triggering condition comprises applying a predetermined temperature and a predetermined pressure.

6. The method of claim 1, wherein applying a triggering condition comprises applying RF pulsing.

7. The method of claim 1, wherein applying a triggering condition comprises applying AC current.

8. The method of claim 1, wherein applying a triggering condition comprises applying DC current.

9. The method of claim 1, wherein when the output voltage of a material is higher than a threshold, one material of the two or more fuel materials is determined to be suitable for the exothermic reaction.

10. The method of claim 9, wherein the threshold is dependent on the exothermic reaction.

11. The method of claim 9, wherein one of the two or more fuel materials is used for calibration purpose and wherein the threshold is set to be the voltage output by this calibration material.

12. A device for selecting one or more fuel materials suitable for producing excess heat in an exothermic reaction, comprising:
a substrate for holding two or more fuel materials; and
a plurality of thermoelectric converters, wherein a respective one of each of the plurality of thermoelectric converters is placed in between a respective fuel material of the two or more fuel materials and the substrate, wherein each respective thermoelectric converter is configured to generate an output voltage that is proportional to the temperature difference between the substrate and the respective fuel material;
wherein the suitability of each of the two or more fuel materials for the exothermic reaction is determined based on the output voltage generated by the thermoelectric converter placed between the substrate and the respective fuel material during a reaction condition.

13. The device of claim 12, wherein the reaction condition includes a pressure and a temperature that trigger the exothermic reaction.

14. The device of claim 12, wherein the device is configured for applying a triggering condition, wherein applying a triggering condition comprises applying an electric field of a predetermined magnitude.

15. The device of claim 12, wherein the device is configured for applying a triggering condition, wherein applying a triggering condition comprises applying an electric field of a predetermined magnitude and polarity.

16. The device of claim 12, wherein the device is configured for applying a triggering condition, wherein applying a triggering condition comprises applying a predetermined temperature and a predetermined pressure.

17. The device of claim 12, wherein the device is configured for applying a triggering condition, wherein applying a triggering condition comprises applying RF pulsing.

18. The device of claim 12, wherein the device is configured for applying a triggering condition, wherein applying a triggering condition comprises applying AC current.

19. The device of claim 12, wherein the device is configured for applying a triggering condition, wherein applying a triggering condition comprises applying DC current.

20. The device of claim 12, wherein each of the two or more fuel materials is determined to be suitable for the exothermic reaction if the output voltage exceeds a threshold.

21. The device of claim 20, wherein the threshold is dependent on the exothermic reaction.

22. The device of claim 20, wherein one of the two or more fuel materials is used for calibration purpose and wherein the threshold is set to be the voltage output by this calibration material.

* * * * *